US012357329B2

(12) United States Patent
Schmitt et al.

(10) Patent No.: US 12,357,329 B2
(45) Date of Patent: Jul. 15, 2025

(54) REAL-TIME COMPOSITION ANALYSIS TECHNIQUES FOR ULTRASONIC ABLATION

(71) Applicant: GYRUS ACMI, INC., Westborough, MA (US)

(72) Inventors: Jeffrey M. Schmitt, Bolton, MA (US); Sergey A. Bukesov, Acton, MA (US); Charles Baker, Rogers, MN (US); Kurt G. Shelton, Bedford, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 877 days.

(21) Appl. No.: 17/446,181

(22) Filed: Aug. 27, 2021

(65) Prior Publication Data

US 2022/0061827 A1 Mar. 3, 2022

Related U.S. Application Data

(60) Provisional application No. 63/071,208, filed on Aug. 27, 2020.

(51) Int. Cl.
*A61B 1/018* (2006.01)
*A61B 5/00* (2006.01)
(Continued)

(52) U.S. Cl.
CPC ........ *A61B 17/22012* (2013.01); *A61B 1/018* (2013.01); *A61B 5/0075* (2013.01);
(Continued)

(58) Field of Classification Search
CPC ......... A61B 2017/22014–22018; A61B 1/018; A61B 5/0075
See application file for complete search history.

(56) References Cited

U.S. PATENT DOCUMENTS 9,421,023 B2 8/2016 Bond et al.
2009/0156900 A1* 6/2009 Robertson .......... A61B 1/00186
600/160
(Continued)

FOREIGN PATENT DOCUMENTS

CN 107242901 A 10/2017
CN 108135496 A 6/2018
(Continued)

OTHER PUBLICATIONS

"International Application Serial No. PCT/US2021/047942, International Preliminary Report on Patentability mailed Mar. 9, 2023", 9 pgs.
(Continued)

*Primary Examiner* — Colin T. Sakamoto
(74) *Attorney, Agent, or Firm* — Schwegman Lundberg & Woessner, P.A.

(57) ABSTRACT

A composition of a biological sample, such as tissue of a patient, can be estimated during an ablation procedure. A composition detector system can include a probe, an illumination source, and a spectrometer. A distal end of a probe can convey mechanical, acoustical, or ultrasonic energy to the tissue to ablate the tissue. The probe can extend through a working channel of a viewing scope. An illumination source can illuminate a portion of the tissue at the distal end of the probe or as the portion is being evacuated and collected for disposal. The illumination can generate response illumination from the portion of the tissue. The spectrometer can receive the response illumination, analyze the response illumination, and provide an estimate of the composition of the portion of tissue.

16 Claims, 13 Drawing Sheets

(51) Int. Cl.
  *A61B 10/04*  (2006.01)
  *A61B 17/22*  (2006.01)
  *A61B 17/00*  (2006.01)
  *A61B 17/32*  (2006.01)

(52) U.S. Cl.
  CPC ............ *A61B 5/0084* (2013.01); *A61B 10/04* (2013.01); *A61B 2017/00061* (2013.01); *A61B 2017/22014* (2013.01); *A61B 2017/320064* (2013.01); *A61B 2017/320069* (2017.08)

(56) References Cited

U.S. PATENT DOCUMENTS

| | | |
|---|---|---|
| 2014/0058244 A1 | 2/2014 | Krocak |
| 2014/0200459 A1 | 7/2014 | Hendriks et al. |
| 2018/0110534 A1 | 4/2018 | Gavala et al. |
| 2018/0263643 A1 | 9/2018 | Shelton et al. |
| 2019/0150703 A1* | 5/2019 | Baker ................ A61B 1/00087 |
| 2019/0201084 A1 | 7/2019 | Shelton, IV et al. |
| 2019/0247680 A1* | 8/2019 | Mayer .................... A61B 17/32 |
| 2020/0000522 A1 | 1/2020 | Chia et al. |

FOREIGN PATENT DOCUMENTS

| | | |
|---|---|---|
| CN | 116113355 A | 5/2023 |
| DE | 112021004467 T5 | 6/2023 |
| JP | H02161937 A | 6/1990 |
| JP | H06261907 A | 9/1994 |
| JP | 2009213589 A | 9/2009 |
| JP | 2017513685 A | 6/2017 |
| JP | 2017522058 A | 8/2017 |
| JP | 2018138166 A | 9/2018 |
| JP | 7640679 | 2/2025 |
| WO | WO-2008041718 A1 | 4/2008 |
| WO | WO-2014181500 A1 | 11/2014 |
| WO | WO-2015164455 A1 | 10/2015 |
| WO | WO-2022047152 A1 | 3/2022 |

OTHER PUBLICATIONS

"Japanese Application Serial No. 2023-513483, Examiners Decision of Final Refusal mailed Jul. 29, 2024", W/English Translation, 9 pgs.

"Japanese Application Serial No. 2023-513483, Notification of Reasons for Rejection mailed Mar. 25, 2024", W/English Translation, 13 pgs.

"Japanese Application Serial No. 2023-513483, Response filed Jun. 24, 2024 to Notification of Reasons for Rejection mailed Mar. 25, 2024", W/English Claims, 23 pgs.

"Japanese Application Serial No. 2023-513483, Voluntary Amendment filed Apr. 21, 2023", w/ English Claims, 16 pgs.

"International Application Serial No. PCT/US2021/047942, International Search Report mailed Dec. 23, 2021", 6 pgs.

"International Application Serial No. PCT/US2021/047942, Written Opinion mailed Dec. 23, 2021", 7 pgs.

"Chinese Application Serial No. 202180052771.3, Office Action mailed Nov. 7, 2024", w/ English translation, 23 pgs.

"Chinese Application Serial No. 202180052771.3, Response filed Feb. 17, 2025 to Office Action mailed Nov. 7, 2024", w/ English Claims, 21 pgs.

"Japanese Application Serial No. 2023-513483, Response filed Nov. 29, 2024 to Examiners Decision of Final Refusal mailed Jul. 29, 2024", w/ english claims, 17 pgs.

"Chinese Application Serial No. 202180052771.3, Response filed Apr. 30, 2025 to Office Action mailed Mar. 6, 2025", w english claims, 18 pgs.

"Chinese Application Serial No. 202180052771.3, Office Action mailed Mar. 6, 2025", W English Translation, 21 pgs.

"Japanese Application Serial No. 2024-209020, Voluntary Amendment filed Mar. 25, 2025", w emglish claims, 17 pgs.

* cited by examiner

REAL-TIME COMPOSITION ANALYSIS TECHNIQUES FOR ULTRASONIC ABLATION

CROSS-REFERENCE TO RELATED APPLICATION

This application claims priority to U.S. Provisional Patent Application No. 63/071,208, filed on Aug. 27, 2020, the contents of which are hereby incorporated by reference in their entirety.

FIELD OF THE DISCLOSURE

The present document relates to ablation techniques for breaking or removing biological tissue, and more particularly, to techniques for analyzing composition of the biological tissue during the ablation procedure.

BACKGROUND OF THE DISCLOSURE

Medical scopes, such as endoscopes and laparoscopes, were first developed in the early 1800s and have been used to inspect inside the body. Medical scopes can include a probe having a distal end with tools and that allow for an optical or electronic image to be captured, and a proximal end with controls for manipulating the tools and devices for viewing the image. A shaft can pass signals and can provide linkages between the proximal and distal ends of the scope. Some medical scopes allow a user to pass tools or treatments down a channel of the shaft, for example, to resect tissue or retrieve objects.

Over the past several decades, several advances have been made in the field of endoscopy, and in particular relating to the breaking up of physiologic calculi in the bile ducts, urinary tract, kidneys, and gall bladder. Physiological calculi, sometimes called stones, in these regions may block ducts and cause a patient a substantial amount of pain. Therapy can include removing or breaking down the stones. Different techniques have been developed to break up stones, including ultrasonic lithotripsy, pneumatic lithotripsy, electro-hydraulic lithotripsy (EHL), and dissolution of calculi using green light, YAG, or holmium lasers.

SUMMARY OF THE DISCLOSURE

Techniques for estimating composition of a biological sample during an ablation procedure are provided. In an example, a composition detector system can include a probe, an illumination source, and a spectrometer. In an example, the probe can extend through a working channel of a viewing scope and can convey mechanical, acoustical, or ultrasonic energy to tissue of a patient to ablate the tissue at a distal end of the probe. A portion of the tissue may be illuminated at the distal end of the probe or as the portion is being evacuated and collected for disposal by the illumination source. The illumination can generate response illumination can be received by the spectrometer. The spectrometer can analyze the response illumination and provide an estimate of the composition of the portion of tissue.

This section is intended to provide an overview of subject matter of the present patent application. It is not intended to provide an exclusive or exhaustive explanation of the invention. The detailed description is included to provide further information about the present patent application.

DETAILED DESCRIPTION

Several devices that use mechanical energy to break a stone into smaller pieces for easier removal from the patient's urologic system have been developed. In certain examples, ultrasonic or acoustic frequency energy can be transmitted down a stiff shaft and delivered by contact to a stone. Many procedures use such a device in a system that also includes a medical scope to allow the shaft to enter confined areas within a patient's body. Such systems can also include a material management system to irrigate the area of interest about the stone and to remove the fragments of the stone as the stone is ablated. Users of ablation equipment have recognized that knowledge of the composition of the stone can assist in providing more efficient therapy. However, conventional techniques require that a portion of the stone or one of the stones be removed from the patient and analyzed outside the ablation system. Such techniques can be time consuming and may have include significant delays between the time a sample is removed from the system and the time a composition analysis is complete. Such delays are often weighed against completing the procedure in a more timely but inefficient manner, without the benefit of the composition information. The present inventors have recognized techniques for analyzing and providing composition information about stone composition within the ablation system and as an ablation procedure proceeds. These new techniques can include a system with in situ analysis or near in situ analysis capabilities. Such techniques can allow an operator of an ablation system to adjust ablation therapy to match the composition of a stone as the stone is being fragmented.

Figure 1:
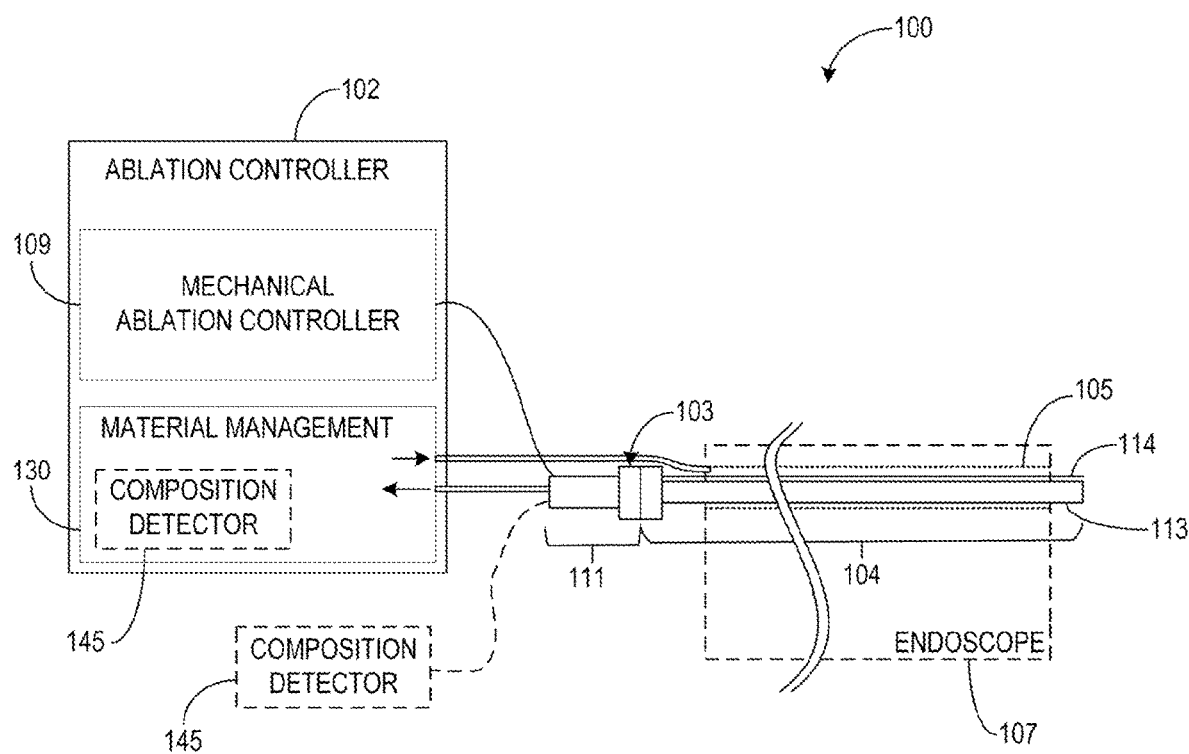
FIG. 1 illustrates generally an example of portions of an ablation system.

FIG. 1 illustrates generally an example of portions of an ablation system 100. The system can include an ablation controller 102, and an ablation instrument 103. In certain examples, a working lumen of a viewing instrument 107, or an access port, can allow for insertion of at least a portion of an ablation probe 104 of the ablation instrument 103 into an internal structure or region of a patient. In certain examples, the viewing instrument can include an endoscope, a laparoscope, or other medical scope. Such scopes can include one or more optical paths, a optical sensor, and additional working lumens. The optical paths can be used to transmit light to the distal end of the viewing instrument, and the optical sensor, such as a camera, can be used to transmit image-type signals to an imaging system coupled to the proximal end of the viewing instrument.

The ablation system 100 can include a mechanical ablation controller 109, a material management system 140. The mechanical ablation controller can include a mechanical energy source, associated controls, and accessories such as to provide the mechanical energy to the ablation instrument 103. The mechanical energy source can deliver acoustic energy at one or more acoustic energy frequencies and at one or more acoustic energy amplitudes. The acoustic energy may be both at sonic frequencies and ultrasonic frequencies. In certain examples, the mechanical energy source may include one or more piezoelectric transducers and mechanical couplings configured to generate acoustic energy at the one or more frequencies.

The material management system 130 can cooperate with the ablation instrument 103 such as to irrigate the distal end of the ablation instrument 103, to aspirate or evacuate material from the distal end of the ablation instrument 103, or to do both. In some examples, the material management system 130 can be part of the endoscope system. In certain examples, the material management system 130 can include a composition detector 145 optionally configured to sample and analyze stone fragments captured by the material management system.

The ablation instrument 103 can include a handle 111, such as can be located at the proximal end of an ablation probe 104. In some examples, a second handle may be located remotely when the ablation procedure is done robotically. The handle 111 can include one or more electrical, mechanical, optical or other interfaces such as for connecting to the mechanical ablation controller 109, or the material management system 140. The handle 111 can include one or more intermediate accessories, such as one or more triggers, buttons, or the like, for actuating the providing of the mechanical energy to the ablation probe 104. The ablation probe 104 can include a tube 113 such as for transmitting the mechanical energy from an electromechanical or other transducer at the handle 111 to a distal end of the tube 113. Such an ablation probe may be referred to as an acoustically transmissive probe. The ablation probe 104 can also include an optical path 114 such as for transmitting optical signals from the distal end of the tube 113 to a composition detector 145 optionally configured to sample and analyze stones in situ at the distal and of the ablation probe 104. In certain examples, the optical fibers of the optical path 114 can be mounted to or integrated with the tube 113. A distal end of the ablation probe 104 can be inserted toward a target site to be used to break up or apply mechanical energy therapy to a stone or biological sample located near the distal end of the tube 113. In certain examples, an internal channel of the tube 113 can provide a channel such as to allow for irrigation of a target region at or near the distal end of the tube 113, or aspiration or evacuation of broken pieces of the obstruction or other target tissue from the patient's body. In certain examples, the gap formed within the working channel 105 but outside the tube 113 can be used for irrigation of a target region at or near the distal end of the tube 113, or aspiration or evacuation of broken pieces of the obstruction or other target tissue from the patient's body. In some examples, the gap formed within the working channel 105 but outside the tube 113 can be used for a complementary material management function compared with the internal channel of the tube 113. For example, in certain examples, when the internal channel of the tube 113 is used for aspiration, the gap between the working channel 105 and the outside the tube 113 can be used for irrigation and vice-versa.

Figure 2:
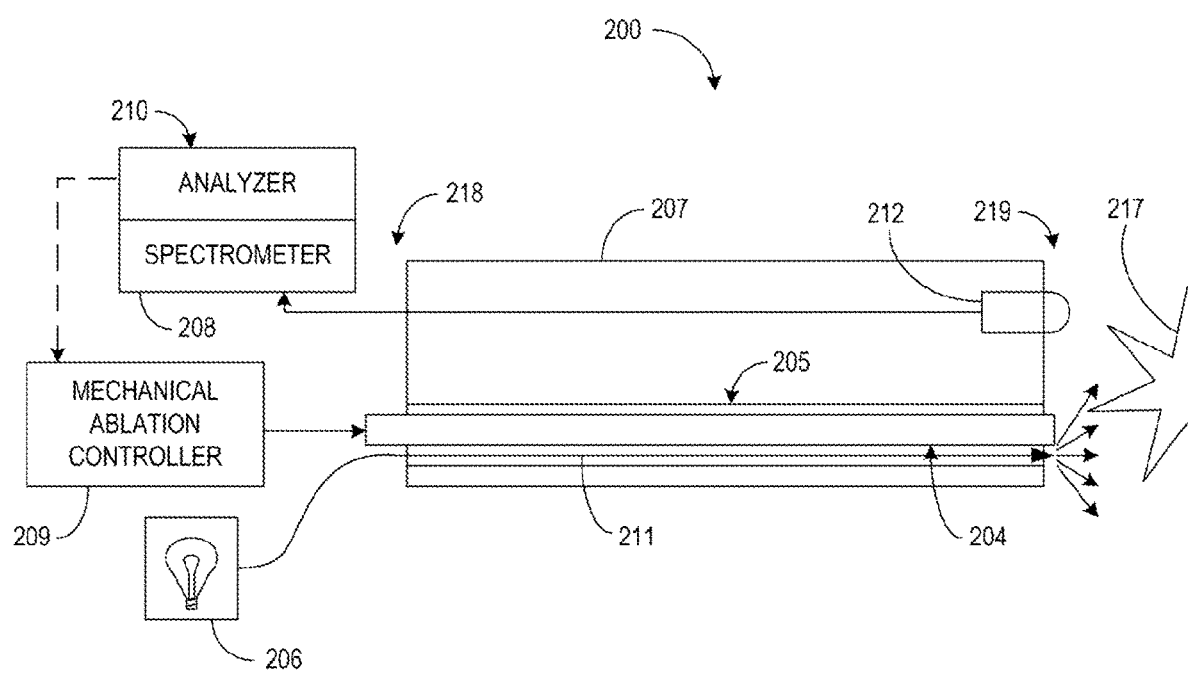
FIG. 2 illustrates generally portions of an example mechanical ablation system for in situ composition detection.

FIG. 2 illustrates generally portions of an example mechanical ablation system 200 for in situ composition detection. Compared to FIG. 1, FIG. 2, FIG. 3, and FIG. 4 illustrate systems specific to sensing and detecting composition of target tissue at the end of the ablation probe 204, 304 rather than when the target tissue is being evacuated for collection as shown in FIGS. 9-12. The mechanical ablation system 200 can include a viewing instrument 207 such as an endoscope or a laparoscope, a first light source 206 separate from the viewing instrument 207, a mechanical ablation controller 209, an ablation probe 204, a spectrometer 208, and an optional spectral analyzer 210. The viewing scope 207 may or may not provide a second light source. The viewing instrument 207 can provide a working channel 205 for insertion of the ablation probe 204 to a target site. In certain examples, the mechanical ablation controller 209 can provide the signaling and the actuation to mechanically ablate a biological specimen 217 located at the distal end 219 of the ablation probe 204. It is understood that the transducer for converting the ablation signals to mechanical energy may be located at the ablation probe 204 or between the ablation probe 204 and the actual control circuit of the mechanical ablation controller 209. Light from the first light source 206 can be transmitted to the distal end 219 of the ablation probe via one or more optical paths 211 of the ablation probe 204. The light of the first light source 206 can illuminate an area about the distal end 219 of the ablation probe 204 including for example, a biological specimen 217 such as a stone. The light of the first light source 206 can produce response illumination captured by an optical sensor 212 of the viewing instrument 207. In some example, the optical sensor 212 can be a camera. The signal from the optical sensor 212 can be received at the spectrometer 208 and the spectrometer 208 can provide spectral information about the biological sample 217 at the distal end 219 of the ablation probe 204. In certain examples, the spectral information can be displayed for the user and the user can base adjustments of the ablation therapy based on the spectral information. In some examples, the optional spectral analyzer 210 can receive the spectral information from the spectrometer 208 and can provide more specific composition information to the user. In some examples, the optional spectral analyzer 210 can determine more specific composition information based on the spectral information received from the spectrometer 208 and can make automatic modifications to the mechanical ablation therapy via the mechanical ablation controller 209, thus providing closed loop control of the ablation therapy.

Figure 3:
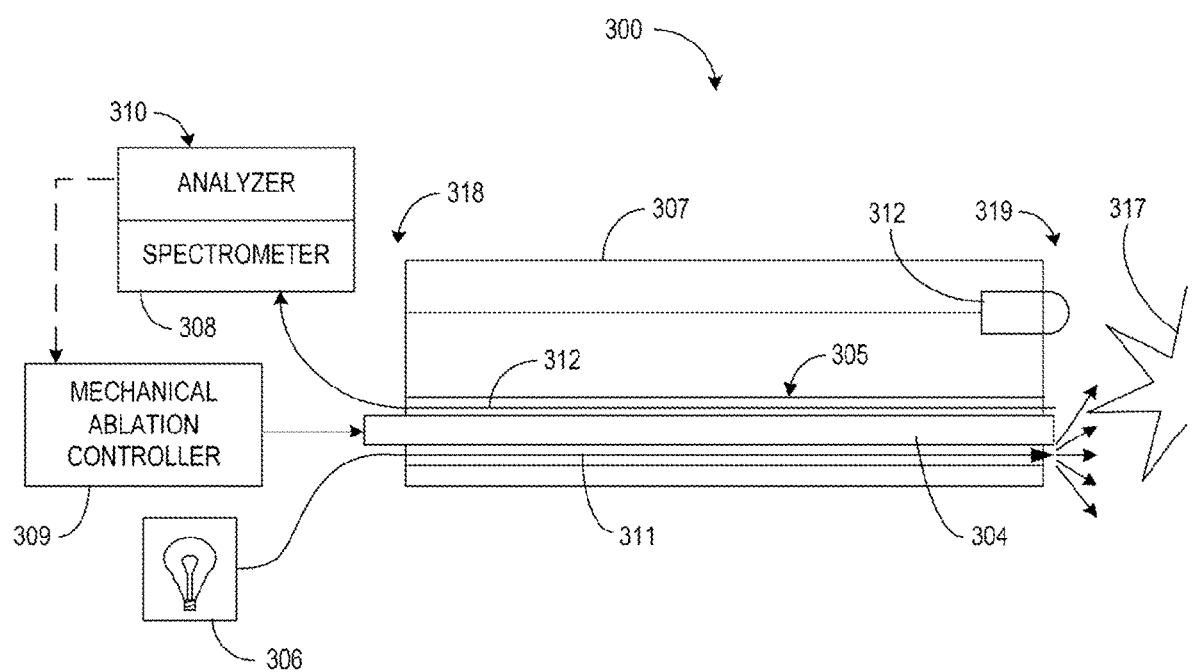
FIG. 3 illustrates generally an example mechanical ablation system for in situ composition detection.

FIG. 3 illustrates generally an example mechanical ablation system 300 for in situ composition detection. The mechanical ablation system 300 can include a viewing instrument 307 such as an endoscope or a laparoscope, a first light source 306 separate from the viewing instrument 307, a mechanical ablation controller 309, an ablation probe 304, a spectrometer 308, and an optional spectral analyzer 309. The viewing scope 307 may or may not provide a second light source. The viewing instrument 307 can provide a working channel 305 for insertion of the ablation probe 304 to a target site. In certain examples, the mechanical ablation controller 309 can provide the signaling and the actuation to mechanically ablate a biological specimen 217 located at the distal end 219 of the ablation probe 304. It is understood that the transducer for converting the ablation signals to mechanical energy may be located at the ablation probe 304 or between the ablation probe 304 and the actual control circuit of the mechanical ablation controller 309. Light from the first light source 306 can be transmitted to the distal end of the ablation probe 304 via one or more optical paths 311 of the ablation probe 304. The light of the first light source 306 can illuminate an area about the distal end 319 of the ablation probe 304 including for example, a biological specimen 317 such as a stone. The light of the first light source 306 can produce response illumination that can be captured by a second optical path 312 of the ablation probe 304. Optionally, the response illumination may be also be captured by the optical sensor 312 of the viewing instrument 307. In some examples, the optical sensor 312 can be a camera. In certain examples, the signal from the optical sensor 312 can be received to provide a visual image for the operator of the mechanical ablation system 300.

The response illumination captured by the second optical path 312 can be received at a spectrometer 308 and the spectrometer 308 can provide spectral information about the biological sample 317 at the distal end 319 of the ablation probe 304. In certain examples, the spectral information can be displayed for the user and the user can base adjustments of the ablation therapy based on the spectral information. In some examples, the optional spectral analyzer 310 can receive the spectral information from the spectrometer 308 and can provide more specific composition information to the user. In some examples, the optional spectral analyzer 310 can determine more specific composition information based on the spectral information received from the spectrometer 308 and can make automatic modifications to the mechanical ablation therapy via the mechanical ablation controller 309, thus providing closed loop control of the ablation therapy.

Figure 4:
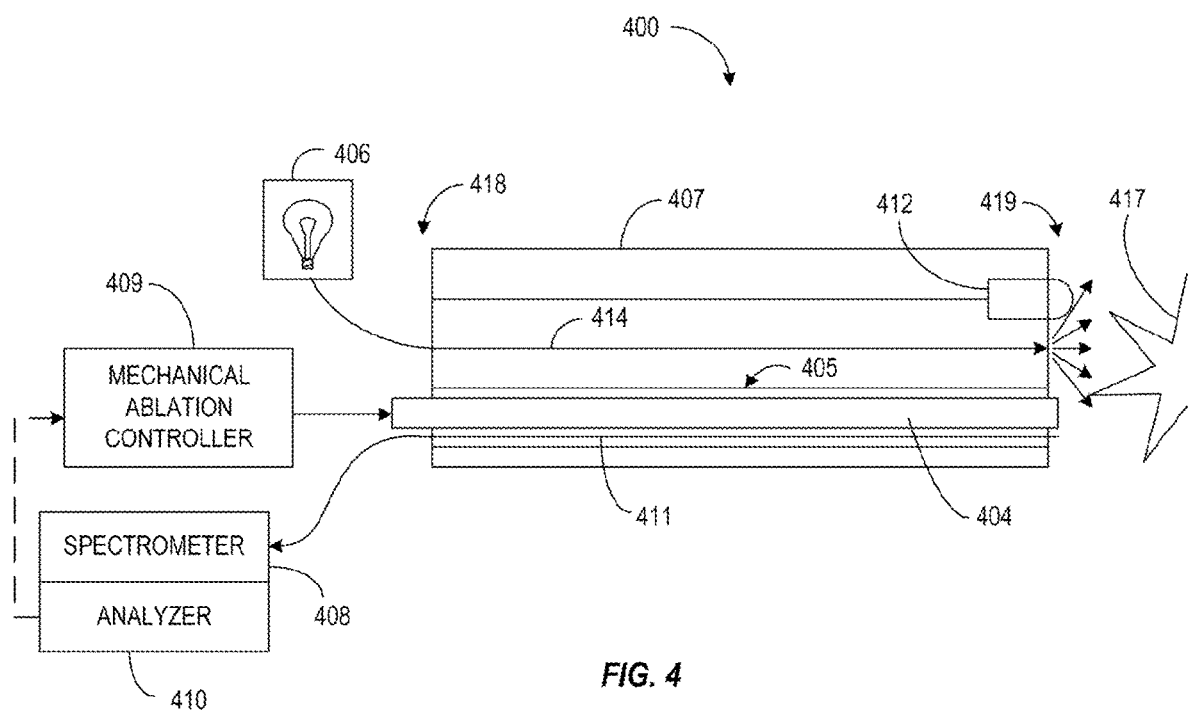
FIG. 4 illustrates generally an example mechanical ablation system for in situ composition detection.

FIG. 4 illustrates generally an example mechanical ablation system 400 for in situ composition detection. The mechanical ablation system 400 can include a viewing instrument 407 such as an endoscope or a laparoscope, a first light source 406, a mechanical ablation controller 409, an ablation probe 404, a spectrometer 408, and an optional spectral analyzer 410. The viewing scope 407 can provide an optical path 414 separate from the ablation probe 404. The viewing instrument 407 can provide a working channel 405 for insertion of the ablation probe 404 to a target site. In certain examples, the mechanical ablation controller 409 can provide the signaling and the actuation to mechanically ablate a biological specimen 417 located at the distal end 419 of the ablation probe 404. It is understood that the transducer for converting the ablation signals to mechanical energy may be located at the ablation probe 404 or between the ablation probe 404 and the actual control circuit of the mechanical ablation controller 409. Light from the light source 406 can be transmitted to the distal end 419 of the viewing instrument 407 via the optical path 414 of the viewing instrument 407. The light of the light source 406 can illuminate an area about the distal end 419 of the ablation probe 404 including for example, the biological specimen 417 such as a stone. The light of the light source 406 can produce response illumination that can be captured by an optical path 411 of the ablation probe 404. Optionally, the response illumination may be captured by the optical sensor 412 of the viewing instrument 407. In some examples, the optical sensor 412 can be a camera. In certain examples, the signal from the optical sensor 412 can be received to provide a visual image for the operator of the ablation system 400.

The response illumination captured by the optical path 411 of the ablation probe 404 can be received at a spectrometer 408 and the spectrometer 408 can provide spectral information about a biological sample 417 at the distal end 419 of the ablation probe 404. In certain examples, the spectral information can be displayed for the user and the user can base adjustments of the ablation therapy based on the spectral information. In some examples, the optional spectral analyzer 410 can receive the spectral information from the spectrometer 408 and can provide more specific composition information to the user. In some examples, the optional spectral analyzer 410 can determine more specific composition information based on the spectral information received from the spectrometer 408 and can make automatic modifications to the mechanical ablation therapy via the mechanical ablation controller 409, thus providing closed loop control of the ablation therapy.

In some examples, the light source 406 can include light-emitting diodes (LEDs). In some examples, the light source 406 can include multiple LED illumination sources and each LED illumination source can provide light of a different color than the other LED illumination sources. In certain examples, activation of the colors of the light source 406 can be sequenced to illuminate the area about the distal end 419 of the ablation probe 404 with light that appears to be white light. However, the sequencing can be synchronized with the spectrometer 408 to reduce noise for spectral measurements at each narrow range of wavelengths associated with each color. In certain examples, spectral measurements and determinations can be made sooner and with more accuracy than of that of a light source providing random light from across the visible spectrum.

FIGS. 5-8 illustrate examples of ablation probes that can provide one or more optical paths for use with the example ablation systems of FIGS. 1-4. In addition to transferring the acoustic energy to fragment target tissue the probes also provide optical pathways to illuminate the target or to collect response illumination for real-time composition analysis of the target tissue. Although the probes of FIGS. 5-8 can be used with the systems of FIGS. 9-12, real-time composition analysis feedback of those systems is based on response illumination gathered from an evacuation path of the material management system. As used herein, "real-time" or "near real-time" relates to a system in which input data (e.g., response illumination) is processed by the system, not outside the system, and the processed information (e.g., composition analysis output) is available as feedback immediately, where any delays between reception of the input and availability of processed feedback are delays generated by the system equipment.

Figure 5:
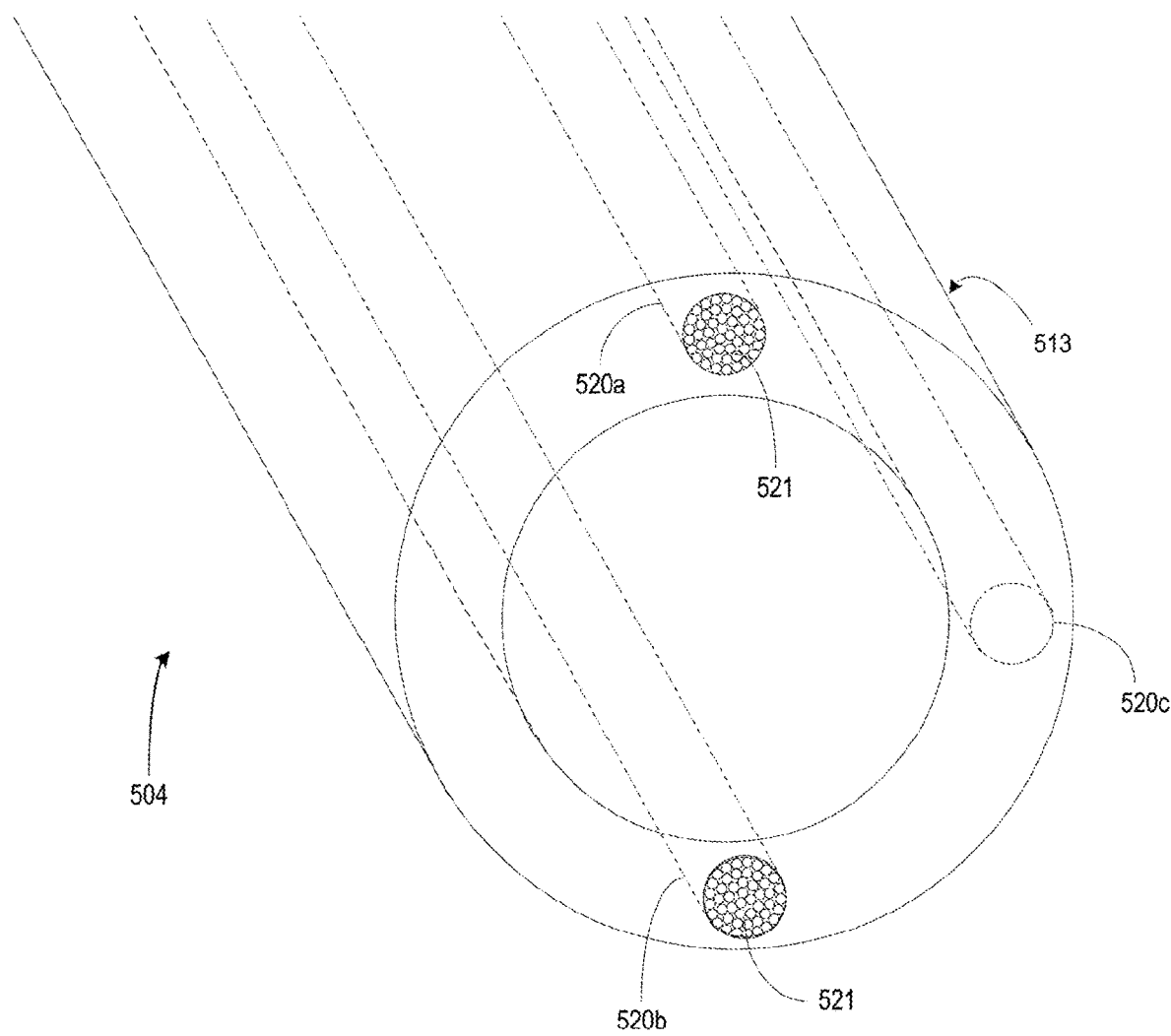
FIGS. 5-8 illustrate examples of mechanical ablation probes that can provide one or more optical paths for use with the example ablation systems of FIGS. 1-4.

FIG. 5 illustrates generally a distal-end view of an example of a portion of an ablation probe 504 that may be used with one or more of the example systems of FIGS. 1-4. The ablation probe 504 can include a metal or other rigid tube 513 such as for delivering mechanical ablation energy from an electromechanical or other transducer to a biological specimen at or near a distal end of the ablation probe 504. Although flexible tubes or semi rigid tubes may be used to navigate meandering paths to a destination, rigid tubes, though less maneuverable, transmit mechanical ablation energy much more efficiently and with less losses than do semi-rigid or flexible tubes. Mechanical ablation of a biological specimen, such as a kidney stone, can include placing the distal end of the tube 513 against the target stone and mechanically vibrating or oscillating the tube 513. The tube 513 can include one or more holes 520 or passages running longitudinally or lengthwise along the tube 513, such as within the sidewalls of the tube 313. FIG. 5 illustrates two holes 520a, 520b within the sidewalls of the tube 513, however the tube 513 can include one or more additional optional holes 520. One or more optical fibers 521 can be located such as to extend within a respective one of the sidewall holes 520a, 520b. The one or more optical fibers can be used to transmit light between the ends of the tube 513 such as for transmitting light to illuminate a distal end of the ablation probe 504 or for transmitting response illumination to a proximal end of the probe 504.

In addition to providing a transmission mechanism for delivering mechanical energy to the target, the tube 513 can provide a central or other longitudinal lumen, such as for irrigating or evacuating the area about the distal end of the probe 504. More than one group or bundle of optical fibers 520c can extend longitudinally via the wall of the tube 513, such as at different circumferential or peripheral locations, or offset about the perimeter defined by the tube by at least 5 degrees or more, for example. In certain examples, the tube 513 can be hollow such as to define an internal channel that can be used to irrigate or evacuate or aspirate material about the distal end of the probe 504.

Figure 6:
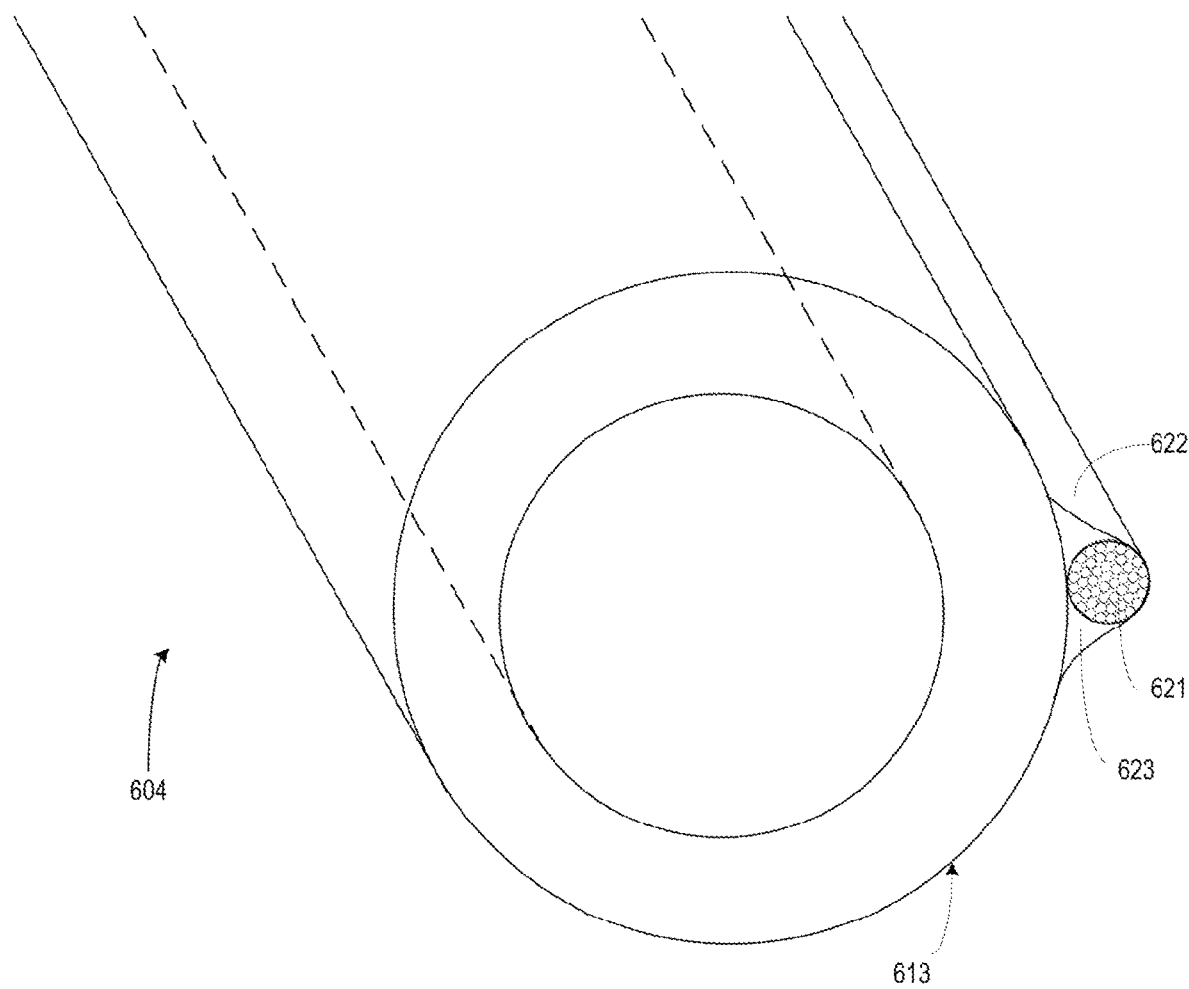

FIG. 6 illustrates generally a distal-end view of an example of a portion of an ablation probe 604 that may be used with one or more of the example systems of FIGS. 1-4. The ablation probe 604 can include a metal or other rigid tube 613 such as for delivering mechanical ablation energy to an obstruction or other target located at or near the distal end of the ablation probe 604 of FIG. 6. One or more optical fibers 621 can extend within or along the tube 613 such as can be used to apply laser energy to an obstruction. For example, the optical fibers 621 can be held against an exterior surface of the tube 613 by a layer of material, a cover material, or a binding material 622, such as a heat-shrink or other shrink wrap type material, for example. Voids between the cover material and the external surface of the tube 613, such as near the optical fibers 621, can be filled with a surgical-grade silicone or other sealant 622. More than one group or bundle of optical fibers 621 can extend longitudinally along the exterior of the tube 613, such as at different circumferential or peripheral locations, or offset about the tube exterior by at least 5 degrees or more, for example. In certain examples, the tube 613 can be hollow such as to define an internal channel such as can also be used to irrigate or evacuate or aspirate material about the distal end of the probe 604.

Figure 7:
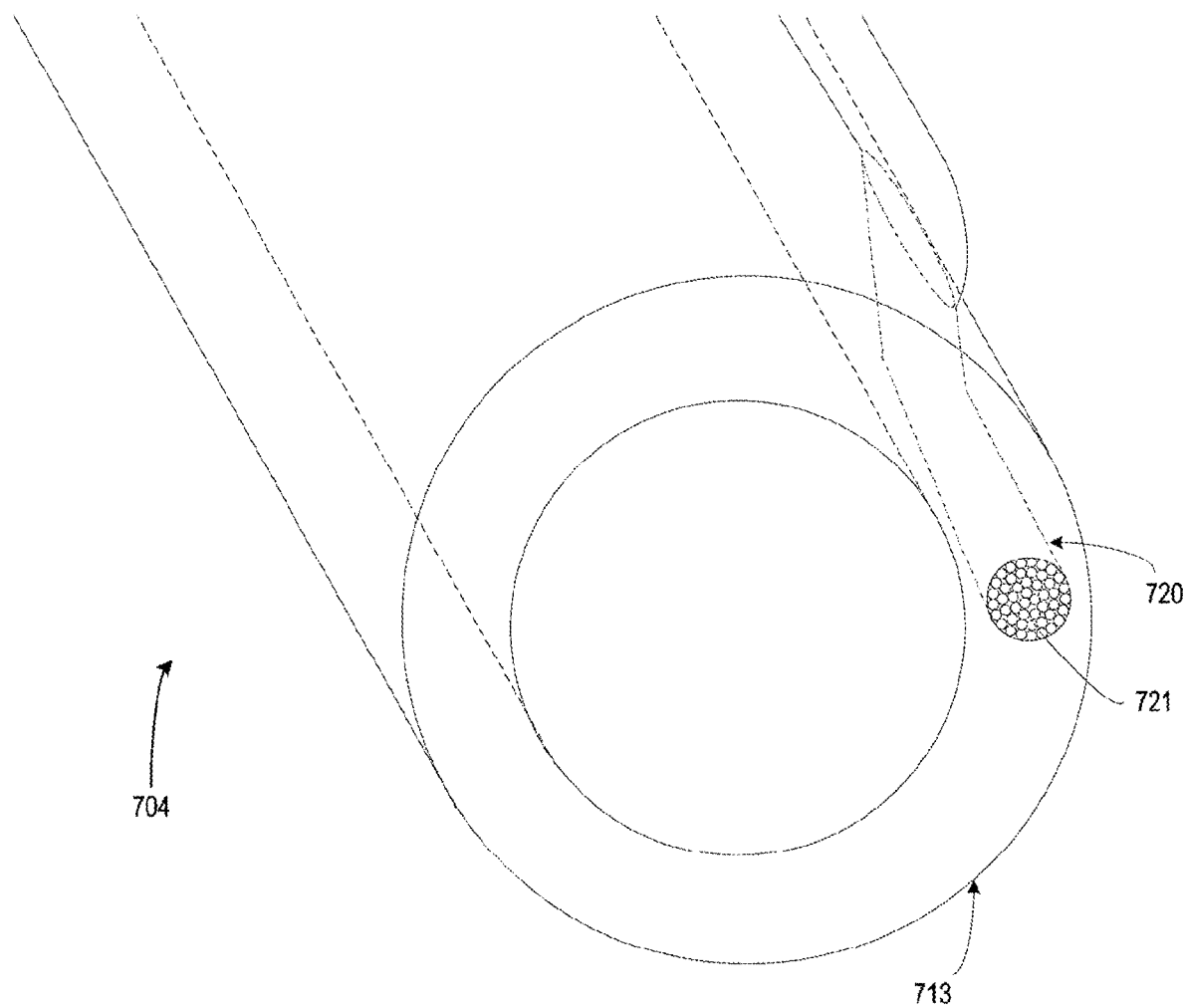

FIG. 7 illustrates generally a distal-end view of an example of a portion of a ablation probe 704 that may be used with one or more of the example systems of FIGS. 1-4. The ablation probe 704 can include a metal or other rigid tube 713 such as for delivering mechanical ablation energy to an obstruction or other target. One or more optical fibers 721 can extend along the tube 713, such as can be used to apply laser energy to an obstruction or other target located at or near a distal end of the probe 704. The bundle or other arrangement of optical fibers 721 can be held against an exterior surface of the tube 713, such as with a cover or binding material, such as a heat-shrink or other shrink wrap material, for example. Near the distal end of the tube 713, the optical fibers 721 can follow a recess in the exterior of the tube 713 and, via a portal, can transition to a hole 720 within the sidewall of the tube 713, such as can provide a passage for the optical fibers 721 to a termination of the hole 720 at the distal end of the tube 713. Voids between the cover material and the external surface of the tube 713, such as near the optical fibers 721, can be filled with a surgical-grade silicone or other sealant. More than one group or bundle of optical fibers 721 can extend along the exterior of the tube 713 before transitioning via a portal to a corresponding hole providing a passage within the sidewall of the tube 713. Such additional portals can be angularly offset from other portals by 5 degrees or more with respect to a centerline of the tube 704. In certain examples, the tube 713 can be hollow such as to define an internal channel such as can also be used to irrigate or evacuate or aspirate material about the distal end of the probe 704.

Figure 8:
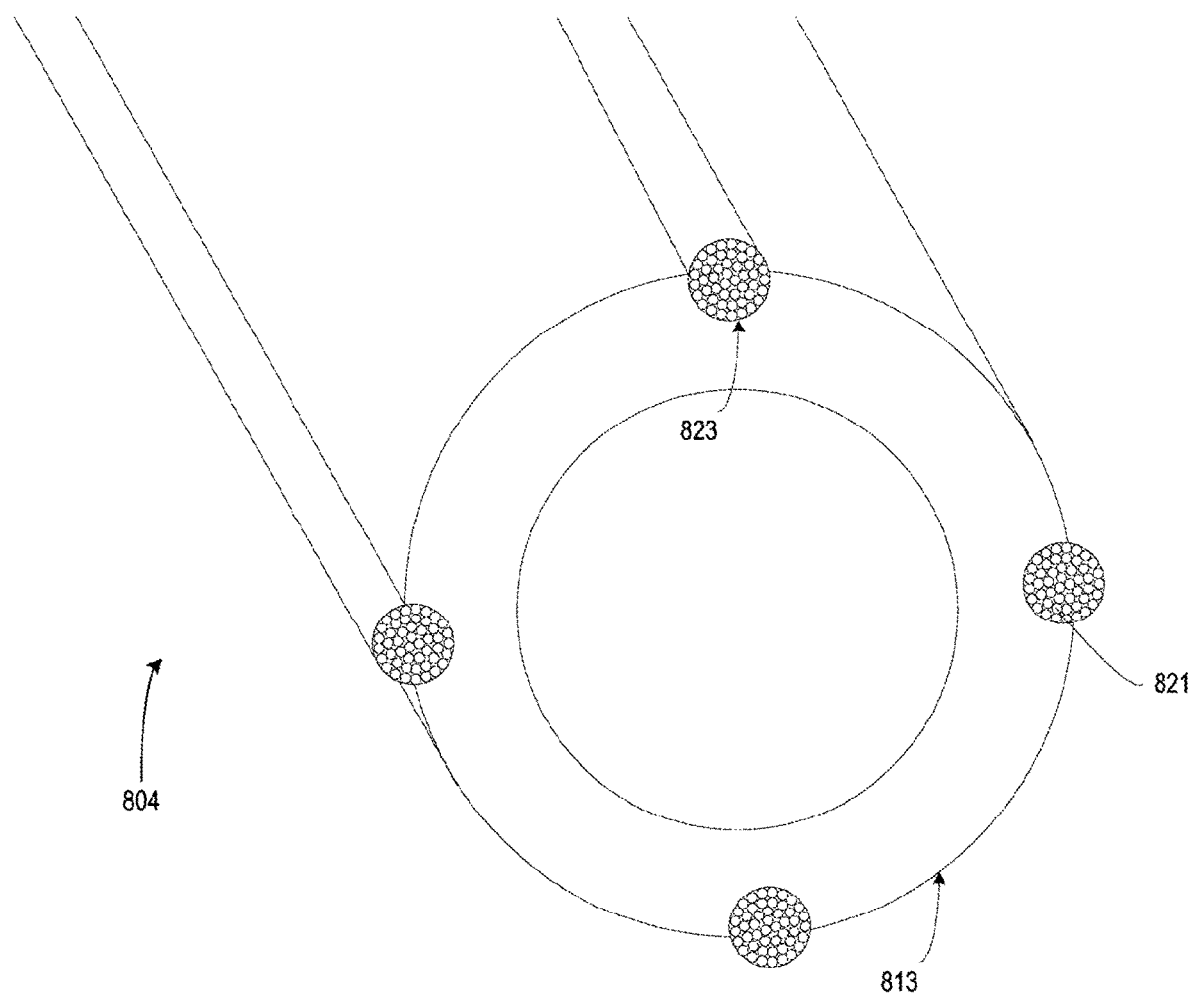

FIG. 8 illustrates generally a distal-end view of an example of a portion of an ablation probe 804 that may be used with one or more of the example systems of FIGS. 1-4. The ablation probe 804 can include a metal or rigid tube 813 such as for delivering mechanical ablation energy to an obstruction. One or more optical fibers 821 can extend along the tube 813, such as can be used to apply laser energy to an obstruction or other target. The tube 813 can include one or more recessed channels 823 on and along an exterior surface of the tube 813, such as to cradle the one or more optical fibers 821. The optical fibers 821 can be held within the channels of the tube 813 such as by a cover or binding material, such as a heat-shrink or other shrink wrap material. Voids between the cover material and the external surface of the tube 813, such as near the optical fibers 821, can be filled with a surgical-grade silicone or other sealant. The multiple-modality probe 804 can include more or fewer bundles of optical fibers 821 than what is shown in FIG. 8.

Figure 9:
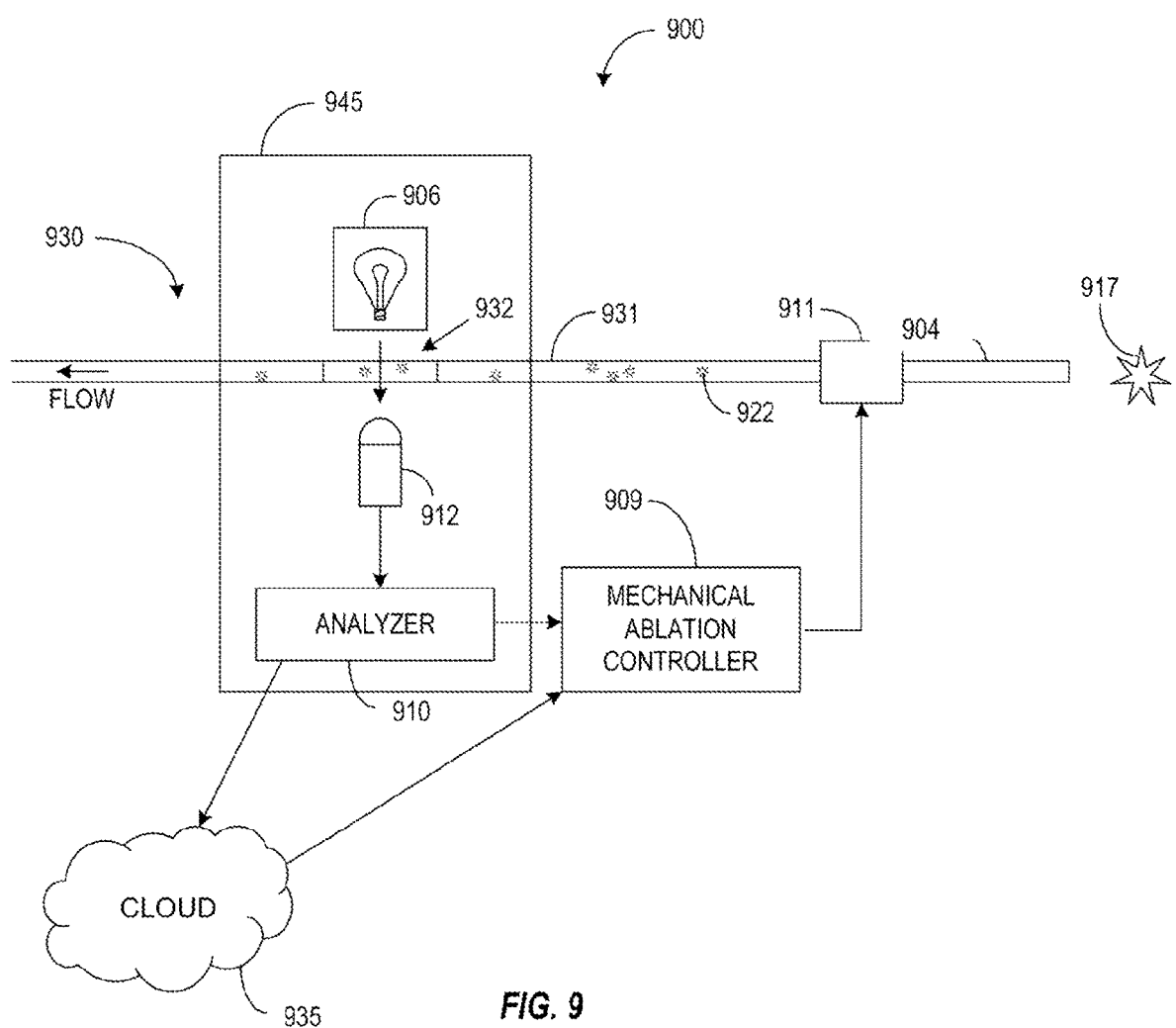
FIG. 9 illustrates a portion of an example mechanical ablation system that includes a composition detector configured to sense ablated material in the material management system and to determine composition information of sensed ablation material.

FIG. 9 illustrates a portion of an example mechanical ablation system 900 that includes a composition detector 945 configured to sense ablated material in the material management system 930 and to determine composition information of sensed ablation material. The portion of the example mechanical ablation system 900 can include a portion of the material management system 930, an ablation probe 904, a light source 906, an optical detector 912, a feedback analyzer 910 and a mechanical ablation controller 909.

The mechanical ablation controller 909 can be used to generate and modulate signals for generating the mechanical ablation energy. In some examples, the mechanical ablation controller 909 can include a transducer for generating the mechanical ablation energy. In some examples, the transducer may reside in the ablation probe 904 or in a handle 911 of the ablation probe. It is understood that the ablation probe 904 may extend through a lumen of a viewing instrument in some examples, such as the examples shown in FIGS. 1-4. The material management system 930 can include an evacuation path 931 to remove irrigation and ablated biological material from the distal end of ablation probe 904. In certain examples, the evacuation path 931 can terminate in a collection system such that ablated material and other materials can be properly contained and disposed of.

The evacuation path 931 can include an optically transparent portion 932. The light source 906 can be placed to allow light to pass through the optically transparent portion 932 of the evacuation path 931. The optical sensor 912 can be placed on an opposite side of the transparent portion 932 from the light source 906 and can have a sensing face focused toward the light source 906. As ablated material 922 passes through the transparent portion 932, the optical sensor 906 can gather information about the composition of the ablated material 922. The feedback analyzer 910 can receive the signal from the optical sensor 906 and can analyze the signal for composition characteristics of the detected ablated material 922. The composition characteristics can include, but are not limited to, size, density, chemical composition, shape, or combinations thereof.

Figure 10A:
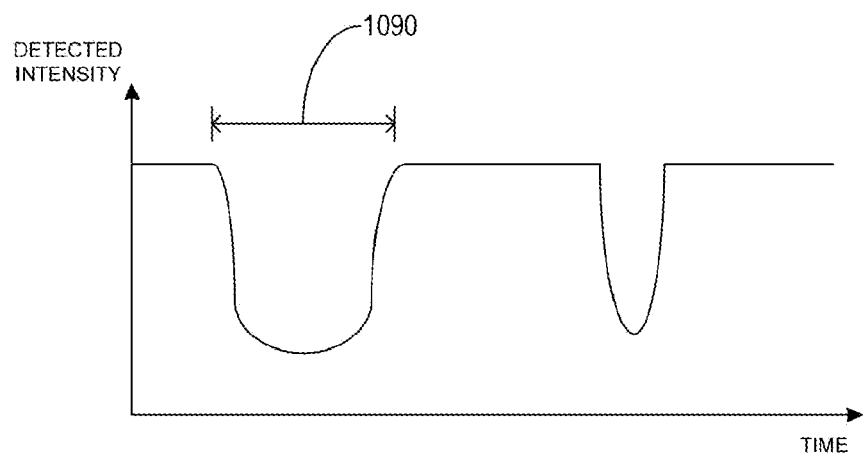
FIGS. 10A and 10B graphically illustrate an example of how a feedback analyzer can determine size and density of a biological sample.
Figure 10B:
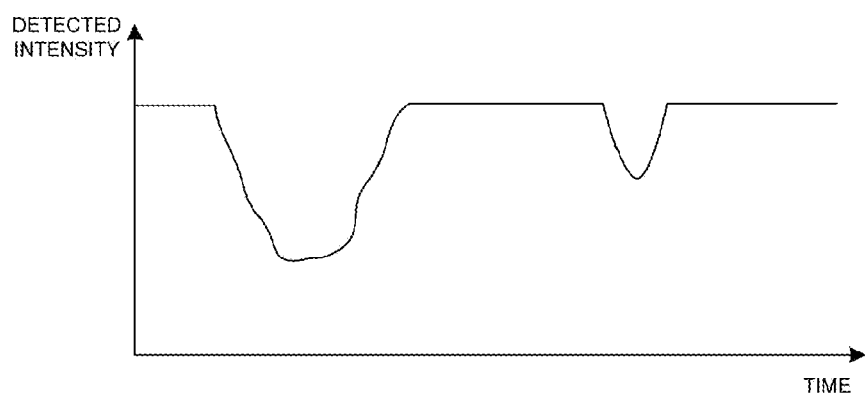

Detection of each composition characteristic can depend on the light source 906 and the sophistication of the optical sensor 912. FIGS. 10A and 10B illustrate an example of how the feedback analyzer can determine size and density. FIGS. 10A and 10B illustrates an intensity signal provided by the optical sensor as the sensor detects two pieces of ablated material passing through the evacuation path between the light source and the optical sensor. Each piece of material is detected via the reduction or dip in intensity of the received light from the light source. Relative size 1090 of each piece can be detected by comparing the time-wise length of each dip. In certain examples, the system can include flowrate information provided by either the evaluation system or by a dedicated sensor. The flow rate information can assist in providing a measured size 1010 for each piece. In some examples, the optical sensor can include an array of light sensors such that an image can be captured and analyzed to provide size information. The pieces illustrated in FIG. 10B do not have dips as large as the dips illustrated in FIG. 10A. The difference between the depth of the dips can indicate that the ablated fragments detected in FIG. 10A are denser than the ablated fragments detected in FIG. 10B. In certain examples, the combination of the intensity level and size of the pieces can be used to estimate absolute density or hardness of the current material being ablated. Such estimates, as discussed below, can then be used to provide real-time feedback to the mechanical ablation controller. Parameters of the mechanical ablation controller can be adjusted based on the feedback such that the current therapy can be applied more efficiently or as efficiently as the mechanical ablation controller is capable of applying the therapy. Parameters of the mechanical ablation controller that may be adjusted include, but are not limited to, driving signal shape (e.g., sinusoid, square wave, saw tooth wave, etc.), frequency (e.g., fixed or continuously sweeping), amplitude (e.g., fixed or continuously sweeping), pulse width and pulse frequency, or combinations thereof.

Referring again to FIG. 9, in certain examples, the optical sensor 906 can provide or actually be a spectrometer. In some examples, the optical sensor 906 may be able to measure flow rate as the edges of the stone fragments 922 move through the field of view of the optical sensor 906. In some examples, the analyzer can integrate the size of the stone fragments 922 over a period of time to estimate the mass or volume of the ablated stone 917. In certain examples, detection information from the optical sensor 906, analysis information from the feedback analyzer 910, or a combination of detection information from the optical sensor 906 and analysis information from the feedback analyzer 910 can be passed to an artificial intelligence application or a machine learning application, such as a cloud 935 based application, for further processing. In such applications, historical procedure information not only from the local procedure location can be combined with other procedure information from regional, national or global procedure locations to further adjust the in-process procedure for more efficient therapy.

Figure 11:
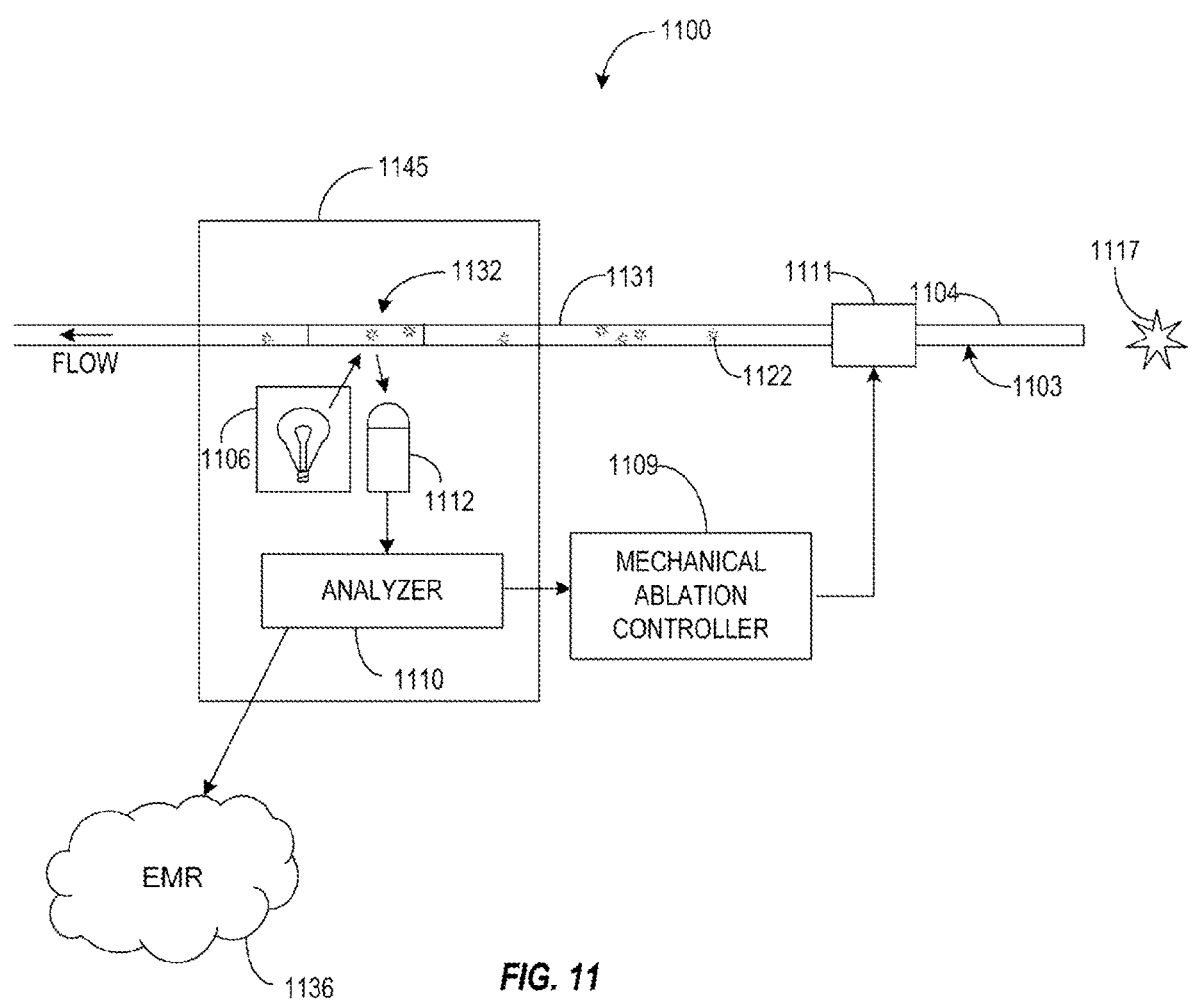
FIG. 11 illustrates a portion of an example mechanical ablation system.

FIG. 11 illustrates a portion of an example mechanical ablation system 1100. The system 1100 is shown ablating biological material 1117, such as a stone, via mechanical ablation and evacuating stone fragments 1122 via an evacuation path 1131 that can include a tube and handle of an ablation probe 1404. The portion of the system 1100 can include a composition detector 1145 configured to sense the ablated material or stone fragments 1122 in the evacuation path 1131 of a material management system 1130 and to determine composition information of the stone fragments 1122. The system can also include the ablation instrument 1103 and an ablation controller 1109. The ablation instrument 1103 can include an ablation probe 1104 and a handle 1111 such as that described above with respect to the example of FIG. 1. It is understood that the ablation probe 904 may extend through a lumen of a viewing instrument in some examples, such as the examples shown in FIGS. 1-4. The evacuation path 1131 can be part of an evacuation system used to irrigate and evacuate ablated material, such as stone fragments 1122, from a patient. The evacuation path 1131 can include a transparent portion 1132 to facilitate composition detection of the stone fragments 1122.

The composition detector 1145 can generally be located along the evacuation path 1131 between the ablation instrument 1407 and the local termination of the evacuation path 1131. Such local termination can include a collection system or a vacuum source for the evacuation path 1131. The composition detector 1145 can include a light source 1406, an optical sensor system 1112. The optical sense system 1112 can detect the stone fragments 1122 and analyze an optical response of a stone fragment 1122 to derive composition information for presentation to the ablation system operator or to adjust therapy of the ablation controller 1409. In certain examples, the optical response can include light of the light source reflected by the stone fragment 1122. In some examples, the optical response can be florescence generated by the stone fragment 1122 in response to light from the light source 1406. In some examples, the sophistication of the optical sensor system 1112 can determine the composition information provided by the composition detector 1145. For example, a less sophisticated optical sensor system 1112 may be able to provide the size or shape of the stone fragment 1122. A more sophisticated optical sensor system 1112 may also provide color details and surface texture details of the stone fragment 1122. As the optical sensor system increases in sophistication, additional composition aspects of the stone fragment 1122 can be determined, and more sophisticated and timely feedback control of the ablation therapy can be achieved. In certain examples, the optical sensor system 1122 can include a spectrometer or spectral analyzer 1140 such that near real-time feedback of the composition of the stone fragment 1122 can be determined and used to adjust ablation therapy to assist in providing more efficient therapy. Such near real-time feedback may include an estimate of hardness which can have a significant impact on modulating ablation energy for efficient delivery of ablation therapy.

In certain examples, the optical sensor system 1112 can provide details about the ablated stone fragments 1122 to an electronic medical record system 1136. Such details can be used to ensure an accurate history for the patient as well as for research and improvement of composition estimates provided by the composition detector 1145.

Figure 12:
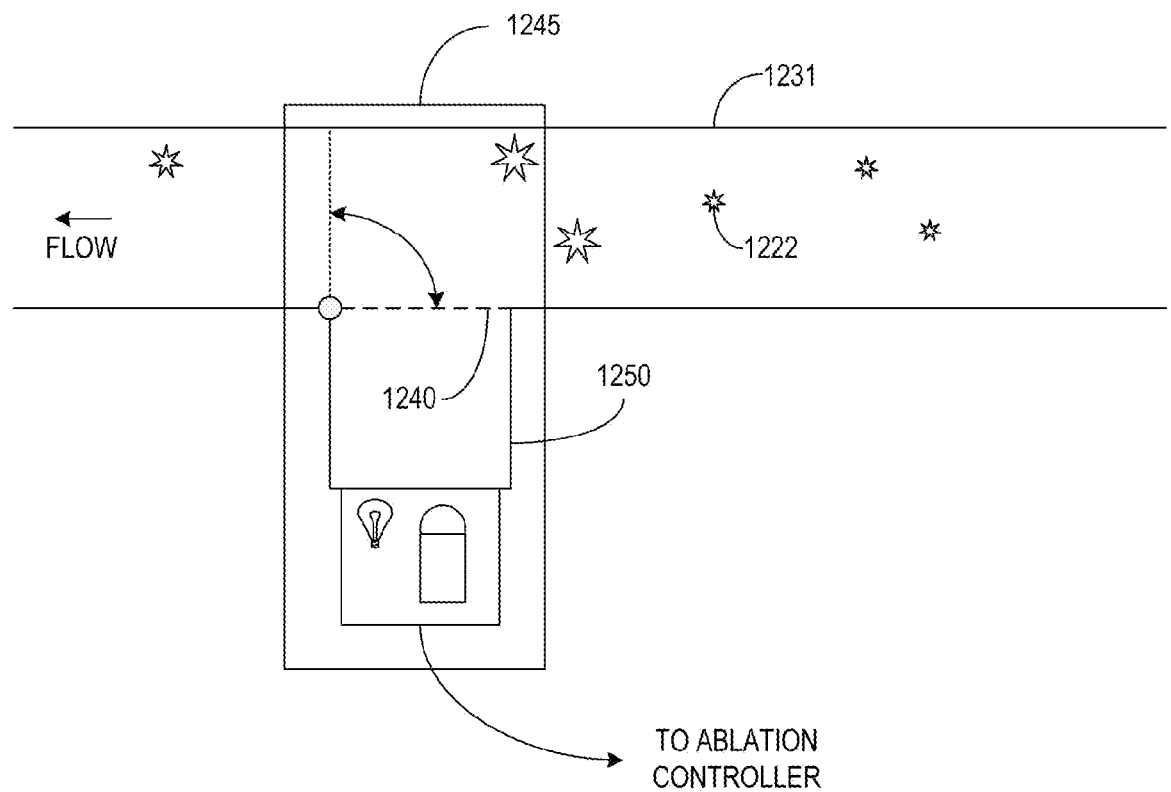
FIG. 12 illustrates a portion of an example composition detector configured to divert ablated material in an evacuation path of an evacuation system for composition analysis.

FIG. 12 illustrates a portion of an example composition detector 1245 configured to divert ablated material 1222 from an evacuation path 1231 of an evacuation system and to determine composition information of the ablation material 1222. Although not limited as such, in some examples, the illustrated composition detector 1245 can be employed as shown and described below or can be a part of a larger system such as the mechanical ablation systems of FIG. 11 or FIG. 1, or in an ablation system that employs another ablation modality such as a laser ablation system. In certain examples, the composition detector 1245 can include a flow control actuator 1241, an optical sensor system 1212, a light source 1206, and an optional collection chamber 1250. In some examples, the flow control actuator 1241 can be used with an upstream sensor and a controller to regulate the flow speed of the evacuation path 1231. In such examples, the actuator 1241 can slow or stop the flow to allow an optical sensor system 1212 to gather image information of a stone fragment 1222, such as a stone fragment sensed upstream by the upstream sensor. In such an application, the composition detector 1245 may not include a collection chamber 1250.

In some examples, the composition detector 1245 includes a collection chamber 1250 such that the flow actuator 1241 can capture stone fragments 1222 and move the captured fragments to the collection chamber 1250. In some examples, collected fragments 1222 can be removed from the collection chamber 1200 for analysis outside the system. In some systems, once in the collection chamber 1250, the optical sensor system 1212 can collect illumination response from the collected fragment(s) 1222 and generate composition information. In certain examples, the optical sensor system 1212 can include a spectrometer or can extract spectral information from the signal provided by an optical sensor of the optical sensor system 1212. In certain examples, the optical sensor system 1212 can include an analyzer 1210 for receiving the spectral information and generating estimates of chemical or material composition of the stone fragment 1222. In some examples, the analyzer can provide estimates of hardness of the stone fragment 1222. In certain examples, the optical sensor system 1212 can provide control signals to an ablation controller to provide closed loop control of the ablation therapy. In some examples, the optical sensor system 1212 can provide raw or analyzed data to a remote medical system, to a remote or cloud-based artificial intelligence system, to a remote or cloud-based machine learning system, or to a combination thereof.

Figure 13:
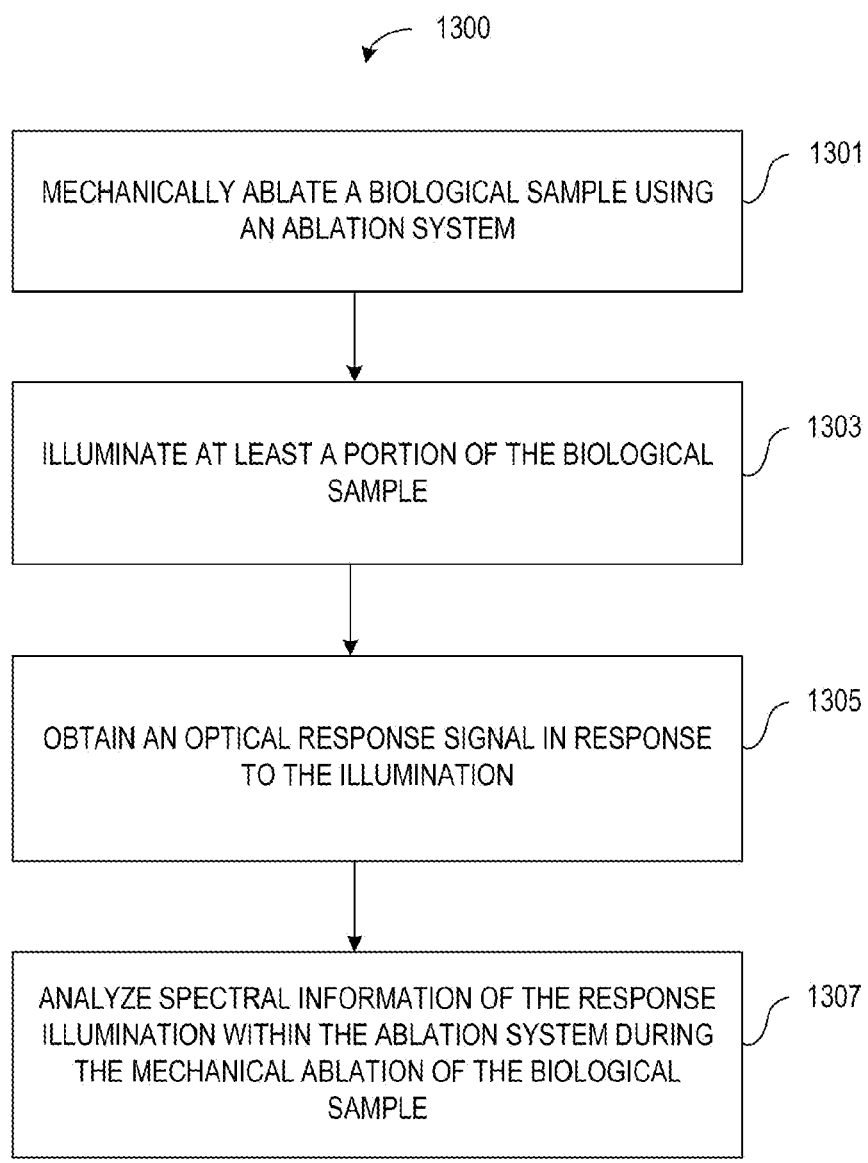
FIG. 13 illustrates generally an example of a method of ablating a biological sample and analyzing the biological sample during the ablation procedure and within the system used for the ablation procedure.

FIG. 13 illustrates generally an example of a method 1300 of ablating a biological sample and analyzing the biological sample during the ablation procedure and within the system used for the ablation procedure. At 1301, a biological sample such as a stone can be mechanically or acoustically treated via an ablation probe of an ablation system. In some examples, the biological sample can be located within a patient and the ablation probe can be extended into the patient through a working channel of a viewing scope instrument. At 1303, at least a portion of the biological sample can be illuminated by an illumination source. At 1305, an optical response signal can be obtained at an optical sensor in response to the illuminating the at least a portion of the sample. At 1307, spectral information of the optical response signal can be analyzed at a location of the patient during the same medical procedure as the treating to determine an indication of a composition of the at least a portion of the sample. In some examples, the illumination and analyzation of the biological sample can take place as the biological sample is ablated within the patient. In some examples, the illumination and analyzation of the biological sample can take place as the biological sample is evacuated from the patient or just after the biological sample is evacuated from the patient but still within an evacuation path of a material management system. The material management system can be used to irrigate the ablation area and evacuate collect and dispose of ablated materials and irrigation materials. In certain examples, estimates of the composition of the biological sample can be used to adjust the ablation therapy

EXAMPLES AND NOTES

In a first example, Example 1, a combined system for both analyzing a biological sample at a location of a patient during a medical procedure, and also treating the biological sample at the location of the patient during the same medical procedure can include an acoustically transmissive probe, configured to extend through a working channel of a viewing scope instrument to acoustically treat the biological sample within the patient at a distal end of the probe; an illumination optical path, configured to illuminate at least a portion of the biological sample; a response optical path, configured to obtain an optical response signal from the at least a portion of the biological sample in response to the illumination; and a spectrometer, configured to analyze, at a location of the patient during the same medical procedure as the treating, spectral information of the optical response signal to determine an indication of a composition of the at least the portion of the sample.

In Example 2, the subject matter of Example 1 includes, wherein the illumination optical path is configured to communicate light toward the distal end of the probe.

In Example 3, the subject matter of any one of Examples 1-2 can optionally further include, wherein illumination optical path extends along the probe through the working channel of the viewing scope instrument.

In Example 4, the subject matter of any one of Examples 1-3 can optionally further include, the viewing scope instrument; and wherein the viewing scope instrument includes the illumination optical path.

In Example 5, the subject matter of any one of Examples 1-4 can optionally further include, wherein the viewing instrument includes a camera configured to detect the optical response signal for communication to the spectrometer.

In Example 6, the subject matter of any one of Examples 1-5 can optionally further include, an evacuation path extending from a distal end of the probe and including a channel of the probe, the evacuation path configured to evacuate the at least a portion of the biological sample away from the distal end of the probe.

In Example 7, the subject matter of any one of Examples 1-6 can optionally further include, wherein the evacuation path is accessed by the illumination optical path and the response optical path to permit the illuminating, the obtaining the optical response, and the analyzing to be performed on the at least a portion of the biological sample while the at least a portion of the biological sample is located in the evacuation path.

In Example 8, the subject matter of any one of Examples 1-7 can optionally further include, a receptacle, configured to receive the at least a portion of the biological sample from the evacuation path, wherein the receptacle is accessed by the illumination optical path and the response optical path to permit the illuminating, the obtaining the optical response, and the analyzing to be performed on the at least a portion of the biological sample while the at least a portion of the sample is located in the receptacle.

In Example 9, the subject matter of any one of Examples 1-8 can optionally further include, wherein at least one or both of the illumination path or the response optical path is coupled to the at least a portion of the biological sample via at least one optically transparent portion.

In Example 10, the subject matter of any one of Examples 1-9 can optionally further include, wherein the spectrometer is configured to receive the optical response signal via the transparent portion.

In Example 11, the subject matter of any one of Examples 1-10 can optionally further include, controller circuitry configured to at least one of establish or adjust an evacuation parameter in response to information including the indication of the composition of the analyzed at least a portion of the biological sample.

In Example 12, the subject matter of any one of Examples 1-11 can optionally further include, controller circuitry configured to at least one of establish or adjust an acoustic treatment parameter in response to information including the indication of the composition of the analyzed at least a portion of the biological sample.

Example 13 is a method of both analyzing a biological sample at a location of a patient during a medical procedure, and also treating the biological sample at the location of the patient during the same medical procedure, the method comprising: acoustically treating the biological sample within the patient via an acoustically transmissive probe extending into the patient through a working channel of a viewing scope instrument; illuminating at least a portion of the sample; obtaining an optical response signal in response to the illuminating; and analyzing, at a location of the patient during the same medical procedure as the treating, spectral information of the optical response signal to determine an indication of a composition of the at least the portion of the sample.

In Example 14, the subject matter of Example 13 can optionally further include, wherein the illuminating includes illuminating the at least the portion of the biological sample via a first optical path extending along the probe through the working channel of the viewing scope instrument.

In Example 15, the subject matter of any one of Examples 13-14 can optionally further include, wherein obtaining the optical response signal includes communicating the optical response signal to a local spectrometer via a camera of the viewing scope instrument.

In Example 16, the subject matter of any one of Examples 13-15 can optionally further include, wherein obtaining the optical response signal includes communicating the optical response signal to a local spectrometer via a second optical path extending along the probe through the working channel of the viewing scope instrument.

In Example 17, the subject matter of any one of Examples 13-16 can optionally further include, evacuating the at least portion of the biological from a distal end of the probe toward a local collection receptacle via an evacuation path that includes at least a portion of a longitudinal channel of the probe; and wherein the illuminating, the obtaining the optical response, and the analyzing are performed on the at least a portion of the sample while the at least a portion of the sample is located in the local collection receptacle.

In Example 18, the subject matter of any one of Examples 13-17 can optionally further include, evacuating the at least portion of the biological from a distal end of the probe via an evacuation path that includes at least a portion of a longitudinal channel of the probe; and wherein the illuminating, the obtaining the optical response, and the analyzing are performed while the at least a portion of the biological sample is being evacuated along the evacuation path.

In Example 19, the subject matter of any one of Examples 13-18 can optionally further include, wherein at least one or both of the illuminating or the obtaining the optical response is performed via at least one optically transparent portion located along the evacuation path.

In Example 20, the subject matter of any one of Examples 13-19 can optionally further include, at least one of establishing or adjusting an evacuation parameter in response to information including the indication of the composition of the analyzed at least a portion of the biological sample.

In Example 21, the subject matter of any one of Examples 13-20 can optionally further include, at least one of establishing or adjusting an acoustic treatment parameter in response to information including the indication of the composition of the analyzed at least a portion of the biological sample.

Example 22 is an ablation instrument for ablating tissue at a distal end of a probe, the ablation instrument including: the probe having a distal end, the distal end configured to extend through a working channel of a viewing instrument; and an evacuation path configured to pass a portion of an ablated tissue, wherein a first portion of the evacuation path includes, the probe; and a target identification system configured to optically sense a portion of the ablated tissue within the evacuation path, measure aspects of the portion, and to provide a first signal representative of the aspects.

In Example 23, the subject matter of Example 22 can optionally further include, wherein the evacuation path includes an optically transparent portion located between a proximal end of the probe and a collection system.

In Example 24, the subject matter of any one of Examples 22-23 can optionally further include, wherein the target identification system includes an illumination source directed toward the optically transparent portion.

In Example 25, the subject matter of any one of Examples 22-24 can optionally further include, wherein the target identification system includes an optical sensor located opposite the illumination source relative to the transparent portion; and wherein the optical sensor is configured to generate the first signal.

In Example 26, the subject matter of any one of Examples 22-25 can optionally further include, wherein the target identification system includes a spectrometer configured to receive response illumination from the optically transparent portion and to generate the first signal.

In Example 27, the subject matter of any one of Examples 22-26 can optionally further include, a flow control configured to receive the first signal and to alter a flow of the portion of the ablated tissue in response to the first signal.

In Example 28, the subject matter of any one of Examples 22-27 can optionally further include, wherein the flow control is configured to capture the portion as a specimen within a specimen chamber coupled with the evacuation path.

Example 29 is a method of ablating tissue comprising: applying energy to the tissue via a distal end of an ablation probe; evacuating a portion of ablated tissue via an evacuation path, the evacuation path including a channel of the ablation probe; optically sensing the portion of ablated tissue as the ablated tissue moves through the evacuation path; and measuring aspects of the portion; and providing a first signal representative of the aspects.

In Example 30, the subject matter of Example 29 can optionally further include, receiving the first signal at a monitor and displaying the aspects.

In Example 31, the subject matter of any one of Examples 29-30 can optionally further include, wherein applying the energy includes applying mechanical ablation energy to the tissue; and wherein the method includes receiving the first signal at a mechanical ablation energy source and adjusting a characteristic of the mechanical ablation energy based on the first signal.

In Example 32, the subject matter of any one of Examples 29-31 can optionally further include, wherein optically sensing the portion include directing illumination through an optically transparent portion of the evacuation path.

In Example 33, the subject matter of any one of Examples 29-32 can optionally further include, wherein optically sensing the portion include directing illumination through an optically transparent portion of the evacuation path toward an optical sensor.

In Example 34, the subject matter of any one of Examples 29-33 can optionally further include, wherein the measuring includes measuring an optical intensity of the illumination at the optical sensor.

In Example 35, the subject matter of any one of Examples 29-34 can optionally further include, wherein the first signal is based on the optical intensity of the illumination.

In Example 36, the subject matter of any one of Examples 29-35 can optionally further include, wherein the optically sensing includes receiving response illumination from the transparent portion of the evacuation path at a spectrometer.

In Example 37, the subject matter of any one of Examples 29-36 can optionally further include, wherein the measuring includes measuring spectral information of the response illumination.

In Example 38, the subject matter of any one of Examples 29-37 can optionally further include, wherein the first signal is based on the spectral information.

In Example 39, the subject matter of any one of Examples 29-38 can optionally further include, adjusting a flow of the ablated tissue through the evacuation path in response to the first signal.

In Example 40, the subject matter of any one of Examples 29-39 can optionally further include, wherein adjusting the flow includes capturing the portion in a specimen chamber coupled to the evacuation path.

Example 41 is an apparatus for sensing ablation material, the apparatus comprising: an evacuation path configured to pass irrigation and ablation material from an ablation probe to a collection system; a light source configured to illuminate the irrigation and ablation material within the evacuation path; an optical sensor focused toward the evacuation path; and a controller configured to receive a first signal from the optical sensor and provide measurement information about the ablation material based on the signal.

In Example 42, the subject matter of Example 41 can optionally further include, a flow control actuator configured to divert flow of the ablation material within the evacuation path.

In Example 43, the subject matter of any one of Examples 41-42 can optionally further include, a specimen reservoir coupled to the evacuation path, the specimen reservoir configured to receive a specimen of the ablation material in response to the flow control actuator diverting flow of the ablation material.

In Example 44, the subject matter of any one of Examples 41-43 can optionally further include, wherein the optical sensor includes a spectrometer.

In Example 45, the subject matter of any one of Examples 41-44 can optionally further include, wherein the controller is configured to provide a second signal representative of the measurement information to an ultrasonic ablation energy source.

In Example 46, the subject matter of any one of Examples 41-45 can optionally further include, wherein the controller is configured to provide a second signal representative of the measurement information to a laser ablation energy source.

Example 47 is a composition identification system comprising: a probe configured to extend through a working channel of a viewing scope and to convey mechanical energy to tissue of a patient to ablate the tissue at a distal end of the probe; an illumination source configured to illuminate at least a portion of the tissue; and a spectrometer configured to receive response illumination from the at least a portion of the tissue and provide composition information about the at least a portion of the tissue.

In Example 48, the subject matter of Example 47 can optionally further include, a first optical media configured to transmit light from the illumination source to the distal end of the probe.

In Example 49, the subject matter of any one of Examples 47-48 can optionally further include, wherein the first optical media extends with the probe through the working channel.

In Example 50, the subject matter of any one of Examples 47-49 can optionally further include, the viewing instrument; and wherein the viewing instrument includes the first optical media.

In Example 51, the subject matter of any one of Examples 47-50 can optionally further include, wherein the viewing instrument includes a camera configured to receive the response illumination and to convey the response illumination to the spectrometer via a first signal.

In Example 52, the subject matter of any one of Examples 47-51 can optionally further include, a second optical media configured to extend with the probe through the working channel, the second optical media configured to convey the illumination response to the spectrometer.

In Example 53, the subject matter of any one of Examples 47-52 can optionally further include, an evacuation path configured to evacuate the at least a portion of the tissue toward a collection system, wherein the evacuation path includes a channel of the probe.

In Example 54, the subject matter of any one of Examples 47-53 can optionally further include, wherein the evacuation path includes an optically transparent portion located between the probe and the collection system.

In Example 55, the subject matter of any one of Examples 47-54 can optionally further include, wherein the illumination source is configured to illuminate the at least a portion of the tissue at the transparent portion.

In Example 56, the subject matter of any one of Examples 47-55 can optionally further include, wherein the spectrometer is configured to receive the response illumination at the transparent portion.

In Example 57, the subject matter of any one of Examples 47-56 can optionally further include, a flow control configured to alter a flow of the at least a portion of the tissue in response to a signal received from a sensor upstream of the spectrometer.

In Example 58, the subject matter of any one of Examples 47-57 can optionally further include, wherein the flow control is configured to capture the portion as a specimen within a specimen chamber coupled with the evacuation path.

Example 59 is a method of operating a composition identification system, the method comprising: mechanically ablating tissue via a probe extending through a working channel of a viewing instrument; illuminating at least a portion of the tissue to provide response illumination; and generating a first signal based on the response illumination, the first signal including spectral analysis information about the composition of the at least a portion of the tissue.

In Example 60, the subject matter of Example 59 can optionally further include, wherein the illuminating includes illuminating the at least a portion of the tissue via a first optical media extending with the probe through the working channel.

In Example 61, the subject matter of any one of Examples 59-60 can optionally further include, wherein generating the first signal includes relaying the illumination response to a spectrometer via a camera of the viewing instrument.

In Example 62, the subject matter of any one of Examples 59-61 can optionally further include, wherein generating the first signal includes receiving the response illumination at a spectrometer via a second optical media extending with the probe through the working channel.

In Example 63, the subject matter of any one of Examples 59-62 can optionally further include, evacuating the at least portion of tissue from a distal end of the probe toward a collection system via an evacuation path, the evacuation path including a channel of the probe.

In Example 64, the subject matter of any one of Examples 59-63 can optionally further include, wherein the illuminating includes illuminating the at least a portion of the tissue via an optically transparent portion of the evacuation path, the optically transparent portion located between a proximal end of the collection system.

In Example 65, the subject matter of any one of Examples 59-64 can optionally further include, wherein generating a first signal based on the response illumination includes receiving the illumination response at a spectrometer located adjacent the transparent portion.

In Example 66, the subject matter of any one of Examples 59-65 can optionally further include, altering a flow of the at least a portion of the tissue in response to a second signal received from a sensor up-flow of the spectrometer.

In Example 67, the subject matter of any one of Examples 59-66 can optionally further include, capturing the at least a portion of the tissue as a specimen within a specimen chamber coupled with the evacuation path.

In Example 68, a system for analyzing and treating a biological sample can include an acoustically transmissive probe to acoustic treatment to the biological sample, the biological sample located within a patient at a distal end of the probe, and an evacuation system configured to evacuate a plurality of portions of the biological sample from an area about the distal end of the probe, the plurality of portions fragmented from the biological sample in response to the acoustical treatment. The evacuation system can include an evacuation path configured to move the plurality of portions to a terminal collection system, and a specimen chamber configured to divert a first portion of the plurality of portions from the evacuation path to provide a specimen of the biological sample.

In Example 69, the system of Example 68 can optionally further include an illumination source configured to illuminate the specimen within the specimen chamber.

In Example 70, the system of any one of Examples 68-69 can optionally include optical sensor system configured to generate spectral information based on response illumination received from the specimen in response to illumination provided by the illumination source.

In Example 71, the system of any one of Examples 68-70 optionally is a spectrometer configured to provide spectral information of the specimen.

In example 72, the system of any one or more of Examples 68-71 optionally includes a controller configured receive the spectral information and to drive the acoustically transmissive probe, the controller further configured to adjust parameters for driving the acoustically transmissive probe in response to the spectral information Example 73 is at least one machine-readable medium including instructions that, when executed by processing circuitry, cause the processing circuitry to perform operations to implement of any of Examples 1-72.

Example 74 is an apparatus comprising means to implement of any of Examples 1-72.

Example 75 is a system to implement of any of Examples 1-72.

Example 76 is a method to implement of any of Examples 1-72.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, the terms "including" and "comprising" are open-ended, that is, a system, device, article, composition, formulation, or process that includes elements in addition to those listed after such a term are still deemed to fall within the scope of subject matter discussed. Moreover, such as may appear in a claim, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of a claim. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. The following aspects are hereby incorporated into the Detailed Description as examples or embodiments, with each aspect standing on its own as a separate embodiment, and it is contemplated that such embodiments can be combined with each other in various combinations or permutations.

What is claimed is:

1. A system for analyzing and treating a biological sample within a patient, the system comprising:

an acoustically transmissive probe configured to extend through a working channel of a viewing scope instrument to acoustically treat the biological sample at a distal end of the probe;

an illumination optical path configured to illuminate at least a portion of the biological sample;

a response optical path configured to obtain an optical response signal from the at least a portion of the biological sample in response to the illumination;

a spectrometer configured to analyze spectral information of the optical response signal to determine an indication of a composition of the at least the portion of the biological sample; and controller circuitry configured to at least one of establish or adjust an acoustic treatment parameter in response to information including the indication of the composition of the analyzed at least a portion of the biological sample.

2. The system of claim 1, wherein the illumination optical path is configured to communicate light toward the distal end of the probe.

3. The system of claim 2, wherein the illumination optical path extends along the probe.

4. The system of claim 2, further comprising an evacuation path that extends from a distal end of the probe and includes a channel of the probe, the evacuation path configured to evacuate the at least a portion of the biological sample away from the distal end of the probe.

5. The system of claim 1, further comprising the viewing scope instrument, the viewing scope instrument including the illumination optical path.

6. The system of claim 5, wherein the viewing instrument includes a camera configured to detect the optical response signal for communication to the spectrometer.

7. The system of claim 5, wherein the illumination optical path extends along the probe through the working channel of the viewing scope instrument.

8. The system of claim 1, further wherein the controller circuitry is configured to establish the acoustic treatment parameter in response to the information including the indication of the composition of the analyzed at least the portion of the biological sample.

9. The system of claim 1, wherein the controller circuitry is configured to adjust the acoustic treatment parameter in response to the information including the indication of the composition of the analyzed at least the portion of the biological sample.

10. The system of claim 1, wherein the acoustic treatment parameter includes at least one of a driving signal shape, frequency, amplitude, pulse width, or pulse frequency of acoustic treatment of the acoustically transmissive probe.

11. The system of claim 1, wherein the controller circuitry is configured to establish or adjust, in real time, the acoustic treatment parameter based on the indication of the composition of the analyzed at least the portion of the biological sample.

12. The system of claim 1, wherein, to determine the indication of the composition of the at least the portion of the biological sample, the spectrometer is configured to determine at least one of a size, shape, surface texture, density, hardness, or color of the at least the portion of the biological sample.

13. The system of claim 1, wherein the acoustically transmissive probe comprises a tube, wherein the illumination optical path and the response optical path are mounted to the tube.

14. The system of claim 1, wherein the acoustically transmissive probe comprises a tube, wherein the illumination optical path and the response optical path are separately integrated with the tube.

15. The system of claim 1, wherein the acoustically transmissive probe comprises a tube, wherein the illumination optical path and the response optical path extend along a portion of the tube and, at a distal portion of the tube, transition through a recess in the tube and terminate at a hole within a sidewall of the tube at a distal end of the tube.

16. The system of claim 1, wherein the spectrometer and the controller circuitry are configured to determine the indication of the composition of the at least the portion of the sample and to adjust the acoustic treatment parameter in response to the information including the indication of the composition of the analyzed at least a portion of the biological sample to provide closed loop control of treatment.

* * * * *

UNITED STATES PATENT AND TRADEMARK OFFICE
CERTIFICATE OF CORRECTION

PATENT NO.        : 12,357,329 B2
APPLICATION NO.   : 17/446181
DATED             : July 15, 2025
INVENTOR(S)       : Schmitt et al.

Page 1 of 1

It is certified that error appears in the above-identified patent and that said Letters Patent is hereby corrected as shown below:

In the Claims

In Column 19, Line 38, in Claim 8, after "claim 1,", delete "further"

Signed and Sealed this
Twenty-sixth Day of August, 2025

Coke Morgan Stewart
*Acting Director of the United States Patent and Trademark Office*